United States Patent
Jang

(10) Patent No.: US 9,526,679 B2
(45) Date of Patent: Dec. 27, 2016

(54) METHOD AND APPARATUS OF MANUFACTURING COSMETIC PRODUCTS FOR REGENERATING SKIN CELL

(71) Applicant: Aphrozone Co., Ltd., Seoul (KR)

(72) Inventor: Eun Mi Jang, Goyang-si (KR)

(73) Assignee: APHROZONE CO., LTD., Seoul (KR)

( * ) Notice: Subject to any disclaimer, the term of this patent is extended or adjusted under 35 U.S.C. 154(b) by 83 days.

(21) Appl. No.: 14/483,210

(22) Filed: Sep. 11, 2014

(65) Prior Publication Data

US 2016/0058680 A1  Mar. 3, 2016

(30) Foreign Application Priority Data

Aug. 28, 2014 (KR) .................. 10-2014-0113052

(51) Int. Cl.
| | | |
|---|---|---|
| *A61L 2/00* | (2006.01) | |
| *C25B 9/00* | (2006.01) | |
| *A61K 8/19* | (2006.01) | |
| *A61K 8/64* | (2006.01) | |
| *A61K 8/97* | (2006.01) | |
| *A61Q 19/00* | (2006.01) | |
| *A61K 8/98* | (2006.01) | |

(52) U.S. Cl.
CPC . *A61K 8/19* (2013.01); *A61K 8/64* (2013.01); *A61K 8/97* (2013.01); *A61K 8/985* (2013.01); *A61Q 19/00* (2013.01); *A61K 2800/20* (2013.01); *A61K 2800/82* (2013.01)

(58) Field of Classification Search
CPC .............. A61L 2/00; A23L 1/293; A23L 2/52; C02F 1/30; C02F 1/46114
USPC 422/1, 28; 204/257, 260; 424/600; 210/251, 198.1, 201–202
See application file for complete search history.

(56) References Cited

U.S. PATENT DOCUMENTS

| | | | | |
|---|---|---|---|---|
| 2007/0258329 A1* | 11/2007 | Winey | .................. | A63B 53/04 |
| | | | | 367/140 |
| 2012/0064182 A1* | 3/2012 | Gohla | ...................... | A61K 8/64 |
| | | | | 424/728 |

FOREIGN PATENT DOCUMENTS

| | | |
|---|---|---|
| KR | 10-2013-0003715 A | 1/2013 |
| KR | 10-2013-0008293 A | 1/2013 |

OTHER PUBLICATIONS

Lee, Eun Young et al., Hypoxia-enhanced wound-healing function of adipose-derived stem cells . . . , Wound Repair and Regeneration, 2009;17, p. 540-547.

(Continued)

*Primary Examiner* — Monzer R Chorbaji
(74) *Attorney, Agent, or Firm* — Paratus Law Group, PLLC

(57) ABSTRACT

A method of manufacturing a cosmetic product for regenerating a skin cell including generating a water into a magnetized hexagonal water through a magnetized hexagonal water generator, separating a body fat stem cell from a body skin through a first extractor to extract a natural protein from a culture medium of a stem cell including the adipose-derived stem cell, extracting at least one skin beneficial ingredient from the culture medium of the stem cell through a second extractor, extracting a plant extract from at least one plant of a pomegranate, red ginseng, liquorice, ginseng seed, milk vetch, poria cocos, scutellaria, portulaca oleracea, pleuropterus multiflorus, angelica, angelica tenuissima, coix, codonopsis, morus alba and cucumber, and mixing the magnetized hexagonal water, natural protein, the at least one skin beneficial ingredient and the at least one plant extract through a mixer to manufacture a cosmetic product for regenerating a skin cell.

5 Claims, 5 Drawing Sheets

(56) References Cited

OTHER PUBLICATIONS

Kim, Won-Serk et al., The wound-healing and antioxidant effects of adipose-derived stem cells, Expert Opinion on Biological Therapy, informa healthcare, 2009;9, p. 879-887.
Kim, Won-Serk et al., Wound healing effect of adipose-derived stem cell . . . , Journal of Dermatological Science, 2007;48, p. 15-24.

* cited by examiner

METHOD AND APPARATUS OF MANUFACTURING COSMETIC PRODUCTS FOR REGENERATING SKIN CELL

CROSS-REFERENCE TO RELATED APPLICATIONS

Pursuant to 35 U.S.C. §119(a), this application claims the benefit of earlier filing date and right of priority to Korean Patent Application No. 10-2014-0113052, filed on Aug. 28, 2014, the contents of which are hereby incorporated by reference herein in their entirety.

BACKGROUND

The present invention relates to a technology of manufacturing a cosmetic product for regenerating a skin cell more particularly to a method and apparatus of manufacturing the cosmetic product for regenerating the skin cell manufacturing a cosmetic product for regenerating the skin cell improving an absorptive power by using a functional water similar to a body water.

A stem cell may differentiate into another cell through a suitable environment and a stimulation and may perform an auto proliferation. An embryonic stem cell (ES cell) separated from an early-stage embryo, an embryonic germ cell (EG cell) separated from a primordial germ cell of an embryonic stage and a multi-potent adult progenitor cell (MAP cell) separated from an adult bone marrow of the stem cell are widely known. The stem cell may be developed to a cell having a distinguishing phenomenon and specialized function so that the stem cell is used for a study object for recovering a function of various organs.

The Korean Patent Publication No. 10-2013-0008293 relates to a method for mass-producing a growth factor using a fetus-derived mesenchymal stem cell from an amniotic fluid with hypoxic culture condition and a composition for regenerating skin using the same and the method includes isolating fetus-derived cell in an amniotic fluid obtained from a pregnant female, sub-culturing the isolated fetus-derived cell in a medium containing a FBS (fetal bovine serum) and a bFGF (basic fibroblast growth factor) to collect the mesenchymal stem cell and culturing the collected mesenchymal stem cell in a hypoxic state. This disclosure may use another source in addition to a bone marrow derived mesenchymal stem cell and may mass-product the growth factor in conditioned medium manufactured by culturing the fetus-derived mesenchymal stem cell in the amniotic fluid with a hypoxic state including a 1% oxygen and additionally culturing in a serum-free medium for three days. This is because a multi-potent mesenchymal stem cell may be obtained by culturing the fetus-derived mesenchymal stem cell in the amniotic fluid.

The Korean Patent Publication No. 10-2013-0003715 relates to a method for manufacturing a culture medium of a fetus-derived mesenchymal stem cell in an amniotic fluid by using a shear stress. The method includes applying a shear stress to a stem cell by scratching the stem cell and culturing the stem cell in serum-free medium for 1-10 days to manufacture a conditioned medium. This disclosure may use the culture medium of the stem cell by applying the shear stress to provide a composite improving a cell growth and a skin regeneration ability.

As described above, because the conventional technology mainly use a purified water to manufacture a composite for regenerating a skin cell when a composite for a skin regeneration is manufactured, a degree forming a cluster of a water and an absorbing power of a skin are low, thereby the composite for regenerating the skin cell does not easily permeate into a skin. At this time, because the composite for regenerating the skin cell manufactured by the conventional technology is easily transubstantiated by an external environment, a trouble occurs in the skin.

SUMMARY OF THE INVENTION

Example embodiments of the present invention propose a method and apparatus of manufacturing a cosmetic product for regenerating a skin cell being capable of manufacturing the cosmetic product for regenerating the skin cell manufacturing a cosmetic product for regenerating the skin cell improving an absorptive power by using a functional water similar to a body water.

In some embodiments, a method of manufacturing a cosmetic product for regenerating a skin cell, the method includes generating a water into a magnetized hexagonal water through a magnetized hexagonal water generator, separating a body fat stem cell from a body skin through a first extractor to extract a natural protein from a culture fluid of a stem cell including the adipose-derived stem cell, extracting at least one skin beneficial ingredient of a peptide, niacinamide, adenosine, arbutin, palmitoyl tripeptide-5, lecithin, squalane, ubiquinone hyaluronic acid, allantoin and collagen from the culture fluid of the stem cell through a second extractor, extracting a plant extract from at least one plant of a pomegranate, red ginseng, liquorice, ginseng seed, milk vetch, poria cocos, scutellaria, portulaca oleracea, pleuropterus multiflorus, angelica, angelica tenuissima, coix, codonopsis, morus alba and cucumber and mixing the magnetized hexagonal water, natural protein, the at least one skin beneficial ingredient and the at least one plant extract through a mixer to manufacture a cosmetic product for regenerating a skin cell.

In one embodiment, generating the magnetized hexagonal water may convert the water into the magnetized hexagonal water by a magnetic force of 10,000 G (gauss) through 13,500 G generated from an N pole of a magnetic substance maintaining a specific distance.

In one embodiment, generating the magnetized hexagonal water may generate the magnetized hexagonal water by using a cluster with an interfacial tension of 40 dyne/cm through 50 dyne/cm and wherein a size of the magnetized hexagonal water generated by using the cluster is lower than that of the magnetized hexagonal water generated by using the water.

In one embodiment, generating the magnetized hexagonal water may simultaneously sterilizes the water and generate the water into the magnetized hexagonal water when the magnetic substance maintaining the specific distance is vibrated by an ultrasonic vibration of 30 Hz through 130 Hz generated at the ultrasonic generator.

In one embodiment, separating the body fat stem cell from the body skin may sub-culture for an embryoid body derived from the body fat stem cell to form a differentiated cell and may simultaneously inhibit a grow of the differentiated cell and culture the differentiated cell to extract a liquid ingredient.

In one embodiment, the liquid ingredient may include a growth factor, procollagen and fibronectin.

In one embodiment, the growth factor may include at least one of an epithelial cell growth factor, fibroblast growth factor, skin cell growth factor, hepatocyte growth factor, insulin growth factor, transformation growth factor and vascular endothelial growth factor.

In one embodiment, the method may further include adjusting a weight of the magnetized hexagonal water, the natural protein, the at least one skin beneficial ingredient and the at least one plant extract to a predetermined mixing ratio and magnetizing and water hexagonalizing the cosmetic product for regenerating the skin cell through the magnetized hexagonal water generator.

In some embodiments, an apparatus of manufacturing a cosmetic product for regenerating a skin cell, the apparatus includes a magnetized hexagonal generator configured to receive a water to generate the water into a magnetized hexagonal water, a first extractor configured to separate a body fat stem cell from a body skin to extract a natural protein from a culture medium of a stem cell including the adipose-derived stem cell, a second extractor configured to extract at least one skin beneficial ingredient of a peptide, niacinamide, adenosine, arbutin, palmitoyl tripeptide-5, lecithin, squalane, ubiquinone hyaluronic acid, allantoin and collagen from the culture medium of the stem cell, a third extractor configured to extract a plant extract from at least one plant of a pomegranate, red ginseng, liquorice, ginseng seed, milk vetch, poria cocos, scutellaria, portulaca oleracea, pleuropterus multiflorus, angelica, angelica tenuissima, coix, codonopsis, morus alba and cucumber and a mixer configured to mix the magnetized hexagonal water, the natural protein, the at least one skin beneficial ingredient and the at least one plant extract to manufacture a cosmetic product for regenerating a skin cell.

In one embodiment, the magnetized hexagonal generator may include a magnetic substance configured to be installed for maintaining a specific distance to form a magnetic force of 10,000 G (gauss) through 13,500 G being generated from an N pole, a water inflow unit configured to receive the water to provide the water to the magnetic substance and an ultrasonic generator configured to vibrate the magnetic substance by an ultrasonic vibration of 30 Hz through 130 Hz simultaneously to sterilize the water and to generate the water into the magnetized hexagonal water.

In one embodiment, the magnetized hexagonal generator may adjust a weight of the magnetized hexagonal water, the natural protein, the at least one skin beneficial ingredient and the at least one plant extract to a predetermined mixing ratio to magnetize and water hexagonalize the cosmetic product for regenerating the skin cell.

In one embodiment, the apparatus may further include a carrier provider configured to provide a carrier being cosmetologically acceptable and a composite generator configured to receive the carrier from the carrier provider to generate a cosmetic material composite containing a cosmetic product for regenerating the skin cell manufactured by the mixer as an effective composite.

In one embodiment, the apparatus may further include a formulation maker configured to manufacture the cosmetic material composite containing a cosmetic product for regenerating the skin cell manufactured by the mixer as the effective composite with the predetermined formation.

The method and apparatus of manufacturing a cosmetic product for regenerating a skin cell and related technologies according to an example embodiment may manufacture the cosmetic product for regenerating the skin cell manufacturing a cosmetic product for regenerating the skin cell improving an absorptive power by using a functional water similar to a body water to improve a degree forming a cluster of a water an absorbing power of a skin are high. Therefore, the cosmetic product for regenerating the skin cell may be easily permeate into a skin and support the skin for recovering to an original state by itself. At this time, a skin trouble may not occur, a skin health and a moisturizing power may strengthen, a synthesis of a skin collagen may be increased to improve a wrinkle, shrink a pore and to improve a skin elasticity.

DETAILED DESCRIPTION

Figure 1:
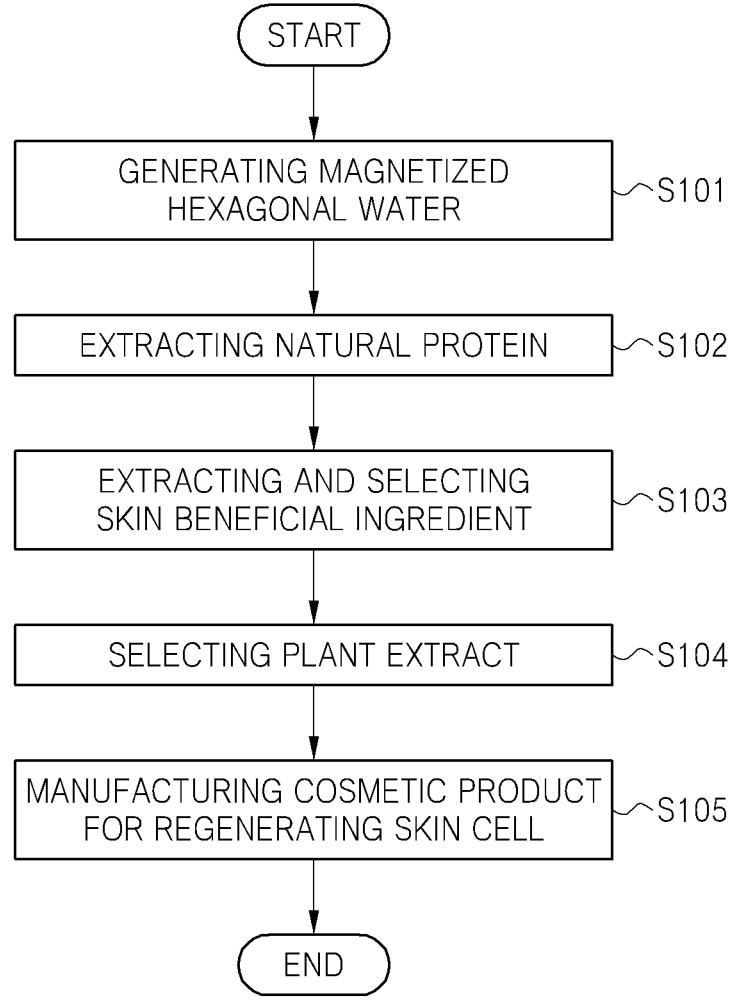
FIG. 1 is a flow chart illustrating a procedure of manufacturing a cosmetic product for regenerating a skin cell according to an example embodiment of the present invention.

Explanation of the present invention is merely an embodiment for structural or functional explanation, so the scope of the present invention should not be construed to be limited to the embodiments explained in the embodiment. That is, since the embodiments may be implemented in several forms without departing from the characteristics thereof, it should also be understood that the described embodiments are not limited by any of the details of the foregoing description, unless otherwise specified, but rather should be construed broadly within its scope as defined in the appended claims. Therefore, various changes and modifications that fall within the scope of the claims, or equivalents of such scope are therefore intended to be embraced by the appended claims.

Terms described in the present disclosure may be understood as follows.

While terms such as "first" and "second," etc., may be used to describe various components, such components must not be understood as being limited to the above terms. The above terms are used to distinguish one component from another. For example, a first component may be referred to as a second component without departing from the scope of rights of the present invention, and likewise a second component may be referred to as a first component.

It will be understood that when an element is referred to as being "connected to" another element, it can be directly connected to the other element or intervening elements may also be present. In contrast, when an element is referred to as being "directly connected to" another element, no intervening elements are present. In addition, unless explicitly described to the contrary, the word "comprise" and variations such as "comprises" or "comprising," will be understood to imply the inclusion of stated elements but not the exclusion of any other elements. Meanwhile, other expressions describing relationships between components such as "between", "immediately between" or "adjacent to" and "directly adjacent to" may be construed similarly.

Singular forms "a", "an" and "the" in the present disclosure are intended to include the plural forms as well, unless the context clearly indicates otherwise. It will be further understood that terms such as "including" or "having," etc., are intended to indicate the existence of the features, numbers, operations, actions, components, parts, or combinations thereof disclosed in the specification, and are not intended to preclude the possibility that one or more other features, numbers, operations, actions, components, parts, or combinations thereof may exist or may be added.

Identification letters (e.g., a, b, c, etc.) in respective steps are used for the sake of explanation and do not described order of respective steps. The respective steps may be changed from a mentioned order unless specifically mentioned in context. Namely, respective steps may be performed in the same order as described, may be substantially simultaneously performed, or may be performed in reverse order.

The terms used in the present application are merely used to describe particular embodiments, and are not intended to limit the present invention. Unless otherwise defined, all terms used herein, including technical or scientific terms, have the same meanings as those generally understood by those with ordinary knowledge in the field of art to which the present invention belongs. Such terms as those defined in a generally used dictionary are to be interpreted to have the meanings equal to the contextual meanings in the relevant field of art, and are not to be interpreted to have ideal or excessively formal meanings unless clearly defined in the present application.

FIG. 1 is a flow chart illustrating a procedure of manufacturing a cosmetic product for regenerating a skin cell according to an example embodiment of the present invention.

Referring to FIG. 1, a magnetized hexagonal water generator generates a water into a magnetized hexagonal water (Step S.101). The magnetized hexagonal water corresponds to a functional water similar to a body fluid. The water flows in the magnetized hexagonal water generator to be magnetized and water hexagonalized by an effect of a strong magnetic force generated from a magnetic substance (e.g., a permanent magnet) installed in the magnetized hexagonal water generator for maintaining a specific distance.

In one embodiment, the magnetized hexagonal water generator may form the strong magnetic force (e.g., 10,000 G (gauss) through 13,500 G) generated from an N pole of the magnetic substance maintaining the specific distance in the magnetized hexagonal water generator to magnetize and water hexagonalize the water flowing therein by the generated magnetic force. The magnetized hexagonal water generator may remove a general bacteria and a colon bacterium by magnetizing and water hexagonalizing the water. The magnetic substance may rotate the water in a 90 degree direction of a magnetic field to smoothly generate the magnetized hexagonal water. At the same time, a kinetic energy is increased by a rotation of an impeller to easily form a cluster of the water. Therefore, the magnetized hexagonal water may increase an amount of the magnetized hexagonal water at a high speed and may reduce a cluster size of the water to improve a permeation power in a body.

Because an interfacial tension of the water is 72 dyne/cm to be bounded to a cell wall and not to pass inside and outside the cell, the magnetized hexagonal water generator may generate the magnetized hexagonal water by using a cluster with a interfacial tension of 40 dyne/cm through 50 dyne/cm to cause the magnetized hexagonal water to pass the cell wall. Herein, a size of the magnetized hexagonal water generated by using the cluster is lower than that of the magnetized hexagonal water generated by using the water.

In one embodiment, the magnetized hexagonal water generator may include a ultrasonic generator generating an ultrasonic wave to the magnetic substance maintaining a specific distance and the distance therein. The ultrasonic generator may generate the ultrasonic vibration to cause the magnetic substance to be vibrated by the ultrasonic vibration. The magnetic substance may generate the ultrasonic vibration of 30 Hz through 130 Hz simultaneously to sterilize the water flowing through the specific distance in the magnetized hexagonal water generator and to generate the water into the magnetized hexagonal water.

In one embodiment, the ultrasonic generator includes an oscillator and a vibrator. The ultrasonic generator may oscillate the oscillator to vibrate the vibrator for causing the vibrator to generate a vibration frequency more than 20,000 per 1 sec. The ultrasonic generator may emit a vibrating magnetic field for causing the magnetic substance to be vibrated by the ultrasonic wave being generated by the vibrator.

When a change of the magnetic field occurs by the vibration, the magnetic substance may cause an energy changing the magnetic field to change a magnetic property of the water flowing through the specific distance in the magnetized hexagonal water generator simultaneously to sterilize the water and to subserve the generation of the magnetized hexagonal water.

A first extractor separates a body fat stem cell to extract a natural protein from a culture medium of a stem cell including the body fat stem cell (Step S102).

The body fat stem cell is very important in a generation and regeneration of a skin, is a source of all body tissue, exists in the skin and causes an aged and damaged skin to be regenerated to a new skin.

The culture medium of the stem cell includes various nutritive ingredients being secreted on culturing the body fat stem cell. The culture medium of the stem cell may regenerate the skin, support a generation of the skin collagen and prevent a pigmentation to transparently and elastically make the skin.

In one embodiment, a differentiated cell may be formed by sub-culturing an embryoid body derived from the body fat stem cell and a liquid ingredient may be separated by simultaneously inhibiting a grow of the differentiated cell and culturing the differentiated cell.

In one embodiment, the first extractor may culture a colony extracted from the body fat stem cell when the differentiated cell is formed as the embryoid body. For example, culturing the colony as the embryoid body may be performed during 5 days through 7 days and a sub-culture of the embryoid body may be performed during 5 days through 10 days to form the differentiated cell having an excellent growth.

In one embodiment, when the differentiated cell is cultured a specific culture medium (e.g., a culture medium of the stem cell), the liquid ingredient may be obtained from a cultured differentiated cell and the culture medium of the stem cell. The liquid ingredient may include a liquid ingredient of the culture medium of the stem cell and a liquid metabolite be generated on culturing the differentiated cell. The liquid ingredient is extracted after the differentiated cell is cultured for one day through five days.

In one embodiment, the liquid ingredient may further a growth factor, a procollagen maintaining the skin elasticity and a fibronectin having a wound healing function by a skin constituent. The growth factor may include a stem cell growth factor for regenerating the skin such as an epithelial cell growth factor, a fibroblast growth factor, a skin cell growth factor. Herein, the epithelial cell growth factor corresponds to a polypeptide being formed by a natural skin regeneration material included in a body from 53 kinds of amino acids, the fibroblast growth factor has functions of promoting a growth of the skin cell and curing the damaged skin and a skin ulcer, the skin cell growth factor has a function of a re-epithelialization promoting a growth and differentiation of a keratinocyte. The growth factor may further include a hepatocyte growth factor, an insulin growth factor, a transformation growth factor and a vascular endothelial growth factor. Herein, the hepatocyte growth factor has functions of inducing a cell activation and curing an injury, the insulin growth factor has a function of promoting a regeneration and a growth of a tissue, the transformation growth factor has a function of adjusting a growth of an immune cell and the vascular endothelial growth factor has functions of inducing growth and differentiation of a cell, promoting a movement of a vascular cell to increase a skin formation.

A second extractor extracts at least one skin beneficial ingredient of a peptide, niacinamide, adenosine, arbutin, palmitoyl tripeptide-5, lecithin, squalane, ubiquinone hyaluronic acid, allantoin and collagen from the culture medium of the stem cell (Step S103).

The skin beneficial ingredient may support a skin whitening, a wrinkle improvement, a skin calming, a skin moisturizing and a skin elasticity increasing. The skin beneficial ingredient may cause a user to select at least one skin beneficial ingredient.

A third extractor extracts a plant extract from at least one plant of a pomegranate, red ginseng, liquorice, ginseng seed, milk vetch, poria cocos, scutellaria, portulaca oleracea, pleuropterus multiflorus, angelica, angelica tenuissima, coix, codonopsis, morus alba and cucumber (Step S104).

The plant extract may support the skin calming, the skin moisturizing and the skin elasticity increasing and may smoothly adjust a balance of oil and moisture and a skin cycle to add a liveliness to the skin. The plant extract may cause a user to select at least one plant extract.

A mixer mixes the magnetized hexagonal water, the natural protein, the at least one skin beneficial ingredient and the at least one plant extract to manufacture a cosmetic product for regenerating a skin cell (Step S105).

In one embodiment, the mixer may adjust a mixing ratio of the magnetized hexagonal water, the natural protein, the at least one skin beneficial ingredient and the at least one plant extract for manufacturing the cosmetic product for regenerating the skin cell having the highest absorptive power of the skin. For example, the mixer may cause the use to adjust by weight 50% of the magnetized hexagonal water, weight 5% of the natural protein, weight 2% of the at least one skin beneficial ingredient, weight 43% of the at least one plant extract.

In one embodiment, the cosmetic product for regenerating the skin cell may be magnetized and water hexagonalized by the magnetized hexagonal water generator to cause the absorptive power of the skin to be increased. The cosmetic product for regenerating the skin cell may include a cosmetic material composite and a carrier may be included in the cosmetic material composite. The cosmetic material composite may further include other composites such as a lubricant, wetting agent, sweeting agent, flavor agent, emulsifying agent, suspension and preserving agent. The cosmetic material composite may be manufactured by various formulations.

For example, the cosmetic material composite may be formulated a suspension, emulsion, paste, gel, cream, lotion, powder, wax or spray type. When the formulation of the cosmetic material composite is the paste, cream or gel type, a carrier of the cosmetic material composite may correspond to an animal oil, vegetable oil, wax, paraffin, starch, tragacanth, cellulose derivative, polyethylene glycol, silicon, bentonite, silica, talc or zinc oxide. When the formulation of the cosmetic material composite is the powder or spray type, the carrier of the cosmetic material composite may correspond to a lactose, talc, silica, aluminum hydroxide, calcium silicate or polyamide powder. When the formulation of the cosmetic material composite is the emulsion type, the carrier of the cosmetic material composite may correspond to an ethanol, isopropanol, ethyl carbonate, ethyl acetate, benzyl alcohol, benzyl benzoate, propylene glycol, butylene glycol, 1,3-butylene glycol, glycerol aliphatic ester, polyethylene glycol or sorbitan fatty acid ester. When the formulation of the cosmetic material composite is the suspension type, the carrier of the cosmetic material composite may correspond to a suspension, microcrystalline cellulose, aluminum metahydroxide, bentonite, agar or tragacanth such as a liquefied diluent (e.g., an ethanol or propylene glycol), ethoxylated isostearyl alcohol and polyoxyethylene sorbitan ester.

In one embodiment, the cosmetic material composite may contain the cosmetic product for regenerating the skin cell as a weight of 0.1% through 10% about a total weight of the cosmetic material composite. For example, the cosmetic product for regenerating the skin cell may be contained as a weight of 0.5% about the total weight of the cosmetic material composite.

Figure 2:
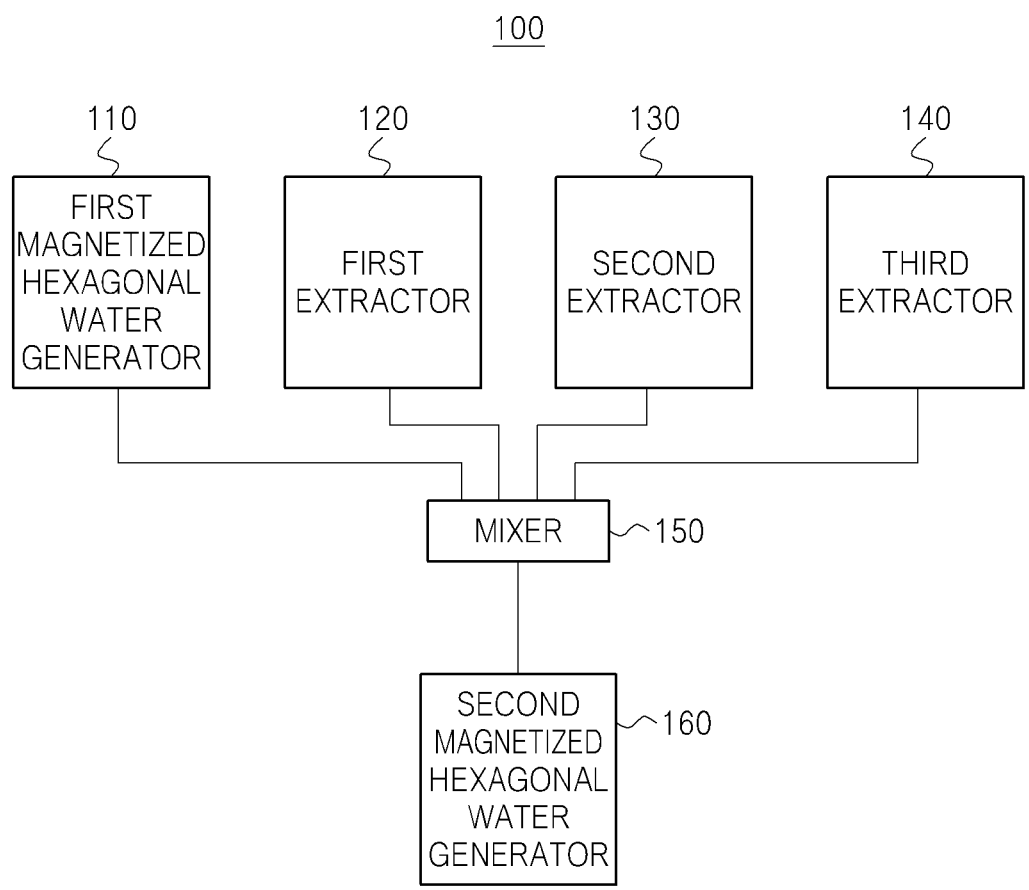
FIG. 2 is a diagram illustrating an apparatus of manufacturing a cosmetic product for regenerating a skin cell in FIG. 1.

FIG. 2 is a diagram illustrating an apparatus of manufacturing a cosmetic product for regenerating a skin cell in FIG. 1.

Referring to FIG. 2, the apparatus of manufacturing cosmetic product for regenerating skin cell 100 includes a first magnetized hexagonal water generator 110, a first extractor 120, a second extractor 130, a third extractor 140 and a mixer 150.

The first magnetized hexagonal water generator 110 includes a water inflow unit and magnetic substance. The water inflow unit receives a water (e.g., a underground water, rock water or abyssal water richly containing a mineral beneficial for the body) generating into the magnetized hexagonal water to provide the water to the magnetic substance and the magnetic substance is installed for maintaining a specific distance in the first magnetized hexagonal water generator 110 to form a strong magnetic force beneficial for the body (e.g., 10,000 G (gauss) through 13,500 G) being generated from an N pole. Thereby, the magnetic substance generates the water provided from the water inflow unit into the magnetized hexagonal water and provides a corresponding magnetized hexagonal water to the mixer 150.

In one embodiment, the first magnetized hexagonal water generator 110 may further include the ultrasonic generator generating an ultrasonic wave. The ultrasonic generator may generate the ultrasonic wave and vibrate the magnetic substance by an corresponding ultrasonic vibration to generate the water flowed in the specific distance into the magnetized hexagonal water having a small cluster.

In one embodiment, the ultrasonic generator oscillation operates at a crystal oscillator to vibrate the vibrator for having for a vibration frequency more than 20,000 per 1 sec. The ultrasonic generator may vibrate magnetic substance by the vibration of a corresponding vibrator to emit the vibrating magnetic field and change a magnetic property of the water flowed in the specific distance simultaneously to sterilize the water and to generate the water into the magnetized hexagonal water.

The first extractor 120 safely separates the body fat stem cell to extract the natural protein from the culture medium of the stem cell obtained by the culture and to provide a corresponding extracted natural protein to the mixer 150.

In one embodiment, the first extractor 120 may subculture for an embryoid body derived from the adipose-derived stem cell. Thereby, when the differentiated cell is formed, the first extractor 120 may simultaneously inhibit a grow of the differentiated cell and culture the differentiated cell to extract a liquid ingredient containing the growth factor, procollagen and fibronectin.

The second extractor 130 extracts at least one skin beneficial ingredient group of the peptide, niacinamide, adenosine, arbutin, palmitoyl tripeptide-5, lecithin, squalane, ubiquinone hyaluronic acid, allantoin and collagen from the culture medium of the stem cell obtained through safely separating the adipose-derived stem cell, selects the at least one skin beneficial ingredient of the at least one extracted skin beneficial ingredient group and provides the at least one selected skin beneficial ingredient to the mixer 150.

The third extractor 140 extracts a plant extract from plant group such as the pomegranate, red ginseng, liquorice, ginseng seed, milk vetch, poria cocos, scutellaria, portulaca oleracea, pleuropterus multiflorus, angelica, angelica tenuissima, coix, codonopsis, morus alba and cucumber, selects at least one plant extract from the extracted plant extract and provides the at least one selected plant extract to the mixer 150.

The mixer 150 mixes the natural protein being provided from the first extractor 120, the at least one skin beneficial ingredient being provided from the second extractor 130 and the at least one plant extract being provided from the third extractor 140 by using the magnetized hexagonal water being provided from the first magnetized hexagonal water generator 110 to manufacture the cosmetic product for regenerating the skin cell.

In one embodiment, the mixer 150 may adjust the weight of the magnetized hexagonal water being provided from the first magnetized hexagonal water generator 110, the natural protein being provided from the first extractor 120, the at least one skin beneficial ingredient being provided from the second extractor 130 and the at least one plant extract being provided from the third extractor 140 according to a predetermined mixing ratio to manufacture the cosmetic product for regenerating the skin cell improving the absorptive power.

In one embodiment, the apparatus of manufacturing cosmetic product for regenerating skin cell 100 may further a second magnetized hexagonal water generator 160. Herein, the mixer 150 may provide a manufactured cosmetic product for regenerating the skin cell to the second magnetized hexagonal water generator 160 thereby the second magnetized hexagonal water generator 160 may magnetize and water-hexagonalize the cosmetic product for regenerating the skin cell being provided from the mixer 150 to generate a cosmetic product for regenerating the skin cell having a higher absorptive power than the absorptive power of the cosmetic product for regenerating the skin cell being provided from the mixer 150.

In one embodiment, the apparatus of manufacturing cosmetic product for regenerating skin cell 100 may further include a composite generator and a carrier provider. The composite generator may generate the cosmetic material composite or a pharmaceutical composite containing the cosmetic product for regenerating the skin cell manufactured from the mixer 150 as an effective composite and the carrier provider may provide a carrier being pharmaceutically or cosmetologically acceptable the composite generator according to a need.

In one embodiment, the apparatus of manufacturing cosmetic product for regenerating skin cell 100 may further include a formulation maker. The formulation maker may manufacture the cosmetic material composite or the pharmaceutical composite containing the cosmetic product for regenerating the skin cell manufactured by the mixer 150 as the effective composite with the predetermined formation.

Figure 3:
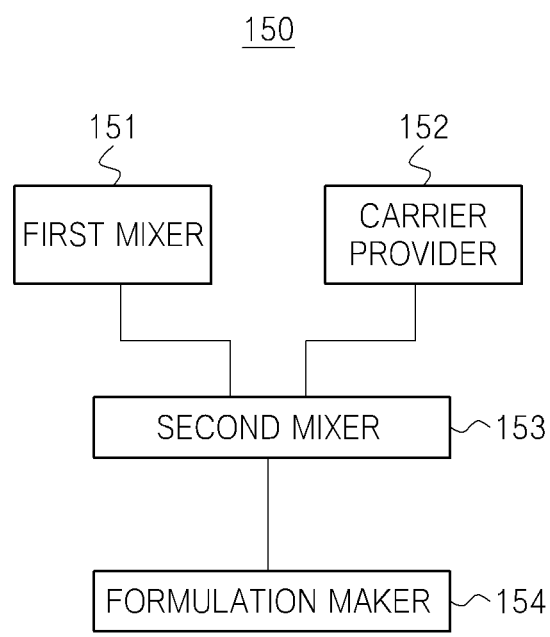
FIG. 3 is a diagram illustrating a mixer in FIG. 1.

FIG. 3 is a diagram illustrating a mixer in FIG. 1.

Referring to FIG. 3, the mixer 150 includes a first mixer 151, a carrier provider 152 and a second mixer 153.

The first mixer 151 mixes the natural protein being provided from the first extractor 120, the at least one skin beneficial ingredient being provided from the second extractor 130 and the at least one plant extract being provided from the third extractor 140 by using the magnetized hexagonal water being provided from the first magnetized hexagonal water generator 110 to manufacture the cosmetic product for regenerating the skin cell and to provide a corresponding manufactured cosmetic product for regenerating the skin cell to the second mixer 152.

The carrier provider 152 provides the carrier being pharmaceutically or cosmetologically acceptable the second mixer 153 according to the need.

In one embodiment, the carrier provider 152 may provide a carrier further including other ingredient such as the a lubricant, wetting agent, sweeting agent, flavor agent, emulsifying agent, suspension and preserving agent to the second mixer 153.

The second mixer 153 mixes the cosmetic product for regenerating the skin cell being provided from the first mixer 151 and the carrier being provided from the carrier provider 152 to generate the cosmetic material composite or the pharmaceutical composite. That is, the second mixer 153 generates the cosmetic material composite or the pharmaceutical composite containing the cosmetic product for regenerating the skin cell as the effective composite.

In one embodiment, the second mixer 153 may mix the carrier being provided from the carrier provider 152 with the cosmetic product for regenerating the skin cell being manufactured in the mixer 150 to generate the cosmetic material composite or the pharmaceutical composite.

In one embodiment, the mixer 150 may further include the formulation maker 154 receiving the cosmetic material composite or the pharmaceutical composite generating the second mixer 153 and manufacturing the cosmetic material composite or the pharmaceutical composite provided from the second mixer 153 by various formulations.

In one embodiment, the formulation maker 154 may be formulated the suspension, emulsion, paste, gel, cream, lotion, powder, wax or spray type.

In one embodiment, the formulation maker 154 may use the carrier such as the animal oil, vegetable oil, wax, paraffin, starch, tragacanth, cellulose derivative, polyethylene glycol, silicon, bentonite, silica, talc or zinc oxide being provided from the carrier provider 152 to form the formulation of the cosmetic material composite as the paste, cream or gel type.

In one embodiment, the formulation maker 154 may use the carrier such as the lactose, talc, silica, aluminum hydroxide, calcium silicate or polyamide powder to form the formulation of the cosmetic material composite as the powder or spray type. Also, the formulation maker 154 may use the carrier such as the ethanol, isopropanol, ethyl carbonate, ethyl acetate, benzyl alcohol, benzyl benzoate, propylene glycol, butylene glycol, 1,3-butylene glycol, glycerol aliphatic ester, polyethylene glycol or sorbitan fatty acid ester to form the formulation of the cosmetic material composite as the emulsion type.

In one embodiment, the formulation maker 154 may use the carrier such as the suspension, microcrystalline cellulose, aluminum meta-hydroxide, bentonite, agar or tragacanth such as a liquefied diluent (e.g., an ethanol or propylene glycol), ethoxylated isostearyl alcohol and polyoxyethylene sorbitan ester to form the formulation of the cosmetic material composite as the suspension type.

Hereinafter, this application will described by one embodiment example, however, this embodiment should not be used for limiting the claim scope.

Figure 4:
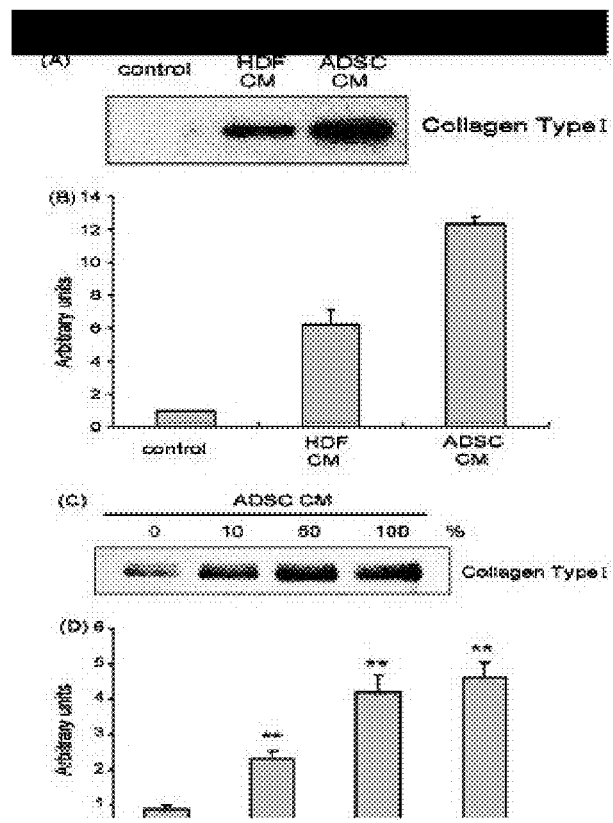
FIGS. 4 through 6 are an example illustrating an experiment for an apparatus of manufacturing a cosmetic product for regenerating a skin cell in FIG. 1.
Figure 5:
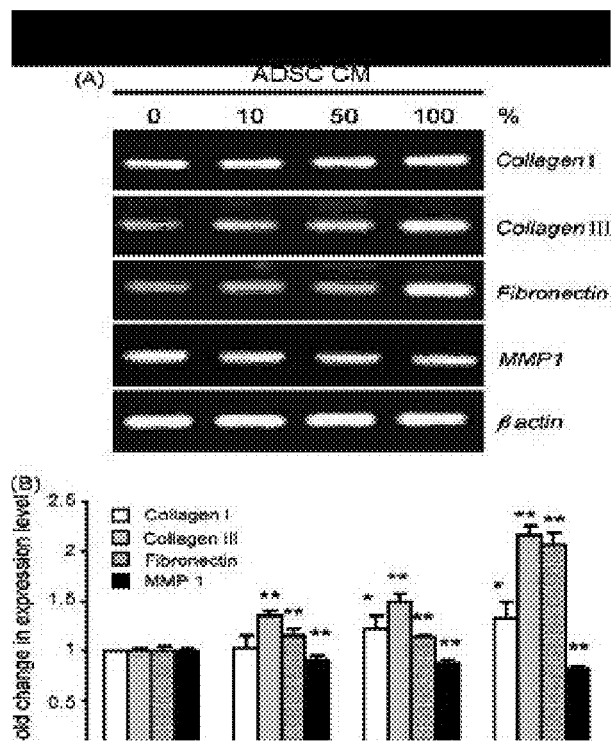
Figure 6:
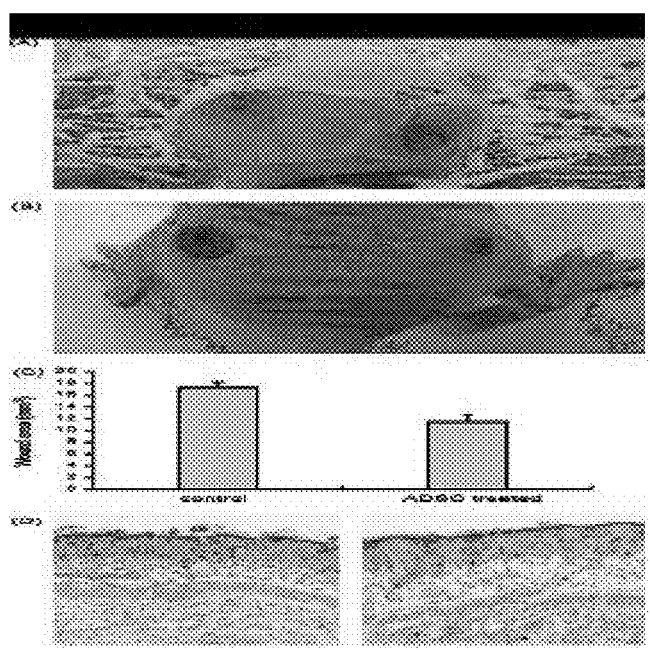

FIGS. 4 through 6 are an example illustrating an experiment for an apparatus of manufacturing a cosmetic product for regenerating a skin cell in FIG. 1.

An embodiment example 1. Wound healing effect of the adipose-derived stem cell

Referring to FIG. 4, a collagen revelation in a culture medium of an adipose-derived stem cell (ADSC-CM) shows a more potent effect than a culture medium of a human dermal fibroblast (HDF-CM) (A) and (B) and the higher a concentration of the culture medium of an adipose-derived stem cell (ADSC-CM) is, the higher the collagen revelation is (C) and (D).

Referring to FIG. 5, an examination of the culture medium of an adipose-derived stem cell (ADSC-CM) is showed based on a biological effect relevant to a migration of the human dermal fibroblast (HDF) and a wound healing analysis.

An mRNA is revealed in a collagen 1, collagen 3, fibronection and MMP1 (Matrix metalloperoteinase-1) detected through a Reverse Transcriptase-Polymerase Chain Reaction (RT-PCR) (A) and is determined by comparing with a β action (B). The revelation of the collagen 1, collagen 3, fibronection and MMP1 (Matrix metalloperoteinase-1) may be increased according to the concentration. That is, the higher the concentration of the culture medium of the adipose-derived stem cell (ADSC-CM) is, the more the wound healing effect is improved.

Referring to FIG. 6, the wound healing effect of the adipose-derived stem cell (ADSC) is showed through a mice experiment. When a day (i.e., 24 hours) is passed after a surgery, an ADSC treatment reduces a wound area and the reduced wound area is smaller than the wound area when any action is not performed.

Although this document provides descriptions of preferred embodiments of the present invention, it would be understood by those skilled in the art that the present invention can be modified or changed in various ways without departing from the technical principles and scope defined by the appended claims.

What is claimed is:

1. A method of manufacturing a cosmetic product for regenerating a skin cell, the method comprising:
   generating a magnetized hexagonal water from a water through a magnetized hexagonal water generator, including:
   applying a magnetic field with a magnetic flux density of 10,000 G (gauss) through 13,500 G in the magnetized hexagonal water generator,
   rotating the water in a direction substantially perpendicular to a direction in which the magnetic field is applied while the magnetic field is applied, and
   generating the magnetized hexagonal water by using a cluster with an interfacial tension of 40 dyne/cm through 50 dyne/cm;
   separating a body fat stem cell from a body skin through a first extractor and extracting a natural protein from a culture medium of a stem cell including the body fat stem cell;
   extracting at least one skin beneficial ingredient of a peptide, niacinamide, adenosine, arbutin, palmitoyl tripeptide-5, lecithin, squalane, ubiquinone hyaluronic acid, allantoin and collagen from the culture medium of the stem cell through a second extractor;
   extracting a plant extract from at least one plant of a pomegranate, red ginseng, liquorice, ginseng seed, milk vetch, poria cocos, scutellaria, portulaca oleracea, pleuropterus multiflorus, angelica, angelica tenuissima, coix, codonopsis, morus alba and cucumber;
   mixing 50% by weight of the magnetized hexagonal water, 5% by weight of the extracted natural protein, 2% by weight of the extracted at least one skin beneficial ingredient, and 43% by weight of the extracted plant extract through a mixer to manufacture a cosmetic product for regenerating a skin cell; and
   magnetizing and water hexagonalizing the cosmetic product for regenerating the skin cell through the magnetized hexagonal water generator.

2. The method of claim 1, wherein the generating the water into the magnetized hexagonal water includes
   simultaneously sterilizing the water and generating the water into the magnetized hexagonal water when a magnetic substance which applies the magnetic field is vibrated by an ultrasonic vibration of 30 Hz through 130 Hz generated at the ultrasonic generator.

3. The method of claim 2, wherein the separating the body fat stem cell from the body skin sub-cultures for an embryoid body derived from the body fat stem cell to form a differentiated cell; and
   simultaneously inhibits a grow of the differentiated cell and cultures the differentiated cell to extract a liquid ingredient.

4. The method of claim 3, wherein the liquid ingredient includes a growth factor, procollagen and fibronectin.

5. The method of claim 4, wherein the growth factor includes at least one of an epithelial cell growth factor, fibroblast growth factor, skin cell growth factor, hepatocyte growth factor, insulin growth factor, transformation growth factor and vascular endothelial growth factor.

* * * * *